(12) United States Patent
Makiyama

(10) Patent No.: US 9,737,200 B2
(45) Date of Patent: Aug. 22, 2017

(54) ENDOSCOPE HAVING A BENDING PORTION WITH INTERSECTING SIGNAL LINE AND WIRE CONDUIT

(71) Applicant: OLYMPUS CORPORATION, Tokyo (JP)

(72) Inventor: Satoshi Makiyama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/239,341

(22) Filed: Aug. 17, 2016

(65) Prior Publication Data

US 2016/0353976 A1 Dec. 8, 2016

Related U.S. Application Data

(63) Continuation of application No. PCT/JP2015/064465, filed on May 20, 2015.

(30) Foreign Application Priority Data

Sep. 1, 2014 (JP) ................................ 2014-177413

(51) Int. Cl.
*A61B 1/005* (2006.01)
*A61B 1/05* (2006.01)
(Continued)

(52) U.S. Cl.
CPC ........ *A61B 1/0057* (2013.01); *A61B 1/00114* (2013.01); *A61B 1/00133* (2013.01);
(Continued)

(58) Field of Classification Search
CPC .............. A61B 1/0057; A61B 1/00188; A61B 1/00133; A61B 1/00163; A61B 1/00071;
(Continued)

(56) References Cited

U.S. PATENT DOCUMENTS 4,989,586 A * 2/1991 Furukawa ................ A61B 1/12
348/65
5,704,899 A * 1/1998 Milo .................... A61B 1/0056
385/107

(Continued)

FOREIGN PATENT DOCUMENTS

EP 1 849 414 A1 10/2007
JP S62-35310 U 3/1987
(Continued)

OTHER PUBLICATIONS

International Search Report dated Aug. 18, 2015 issued in corresponding International PCT Application No. PCT/JP2015/064465.

*Primary Examiner* — John P Leubecker
(74) *Attorney, Agent, or Firm* — Scully, Scott, Murphy & Presser P.C.

(57) ABSTRACT

An endoscope achieves favorable advancing and retracting motion without causing disturbance in displacement of built-in components in bending of a bending tube by covering, out of an image pickup cable and a conduit that are cross-symmetrical built-in components disposed to intersect with each other in a radial direction of the bending tube, an outer circumference of the conduit with a second heat-shrinkable tube serving as a protective member, and removing the second heat-shrinkable tube from a partial region that includes a region (an intersection region) where the image pickup cable and the conduit intersect with each other, even when the built-in components in the bending tube are intersected with each other.

3 Claims, 7 Drawing Sheets

(51) Int. Cl.
*A61B 1/00* (2006.01)
*A61B 1/008* (2006.01)
*A61B 1/012* (2006.01)
*G02B 23/24* (2006.01)

(52) U.S. Cl.
CPC ...... *A61B 1/00163* (2013.01); *G02B 23/2476* (2013.01); *A61B 1/008* (2013.01); *A61B 1/00117* (2013.01); *A61B 1/00119* (2013.01); *A61B 1/00188* (2013.01); *A61B 1/012* (2013.01); *G02B 23/2423* (2013.01)

(58) Field of Classification Search
CPC ............... A61B 1/008; A61B 1/00098; A61B 2017/00323; G02B 23/2476; G02B 23/2423; G02B 23/2438
USPC .......................................... 600/128, 130, 110
See application file for complete search history.

(56) References Cited

U.S. PATENT DOCUMENTS

| | | | |
|---|---|---|---|
| 5,840,016 A | 11/1998 | Kitano et al. | |
| 6,923,757 B2* | 8/2005 | Abe | A61B 1/00071 600/101 |
| 7,918,785 B2* | 4/2011 | Okada | A61B 10/04 600/104 |
| 8,641,606 B2* | 2/2014 | Ichihashi | A61B 1/00048 600/110 |
| 2001/0018552 A1* | 8/2001 | Akiba | A61B 1/00188 600/146 |
| 2002/0123664 A1* | 9/2002 | Mitsumori | A61B 1/00096 600/130 |
| 2008/0194914 A1* | 8/2008 | Iwasaki | A61B 1/00188 600/167 |
| 2013/0150666 A1* | 6/2013 | Otawara | A61B 1/00078 600/104 |
| 2015/0265137 A1* | 9/2015 | Takahashi | G02B 23/24 600/110 |

FOREIGN PATENT DOCUMENTS

| | | |
|---|---|---|
| JP | H1-87702 U | 6/1989 |
| JP | 09-122069 A | 5/1997 |
| JP | 2000-241634 A | 9/2000 |
| JP | 2002-306490 A | 10/2002 |
| JP | 2002-345740 A | 12/2002 |
| JP | 2005-342129 A | 12/2005 |
| JP | 2006-218157 A | 8/2006 |
| JP | 2006-288759 A | 10/2006 |
| JP | 2007-037786 A | 2/2007 |
| JP | 2012-110426 A | 6/2012 |
| WO | 2006/082692 A1 | 8/2006 |

* cited by examiner

ENDOSCOPE HAVING A BENDING PORTION WITH INTERSECTING SIGNAL LINE AND WIRE CONDUIT

CROSS REFERENCE TO RELATED APPLICATION

This application is a continuation application of PCT/JP2015/064465 filed on May 20, 2015 and claims benefit of Japanese Application No. 2014-177413 filed in Japan on Sep. 1, 2014, the entire contents of which are incorporated herein by this reference.

BACKGROUND OF THE INVENTION

1. Field of the Invention

The present invention relates to an endoscope that includes a bending portion on a distal end side of an insertion section.

2. Description of the Related Art

An endoscope is conventionally widely used in a medical field and other fields. For example, the endoscope is used, through insertion of an elongated insertion section into a subject, in observation of a target site in the subject, and in various kinds of treatment with use of treatment instruments that are inserted into a treatment instrument channel as necessary. The endoscope of this type typically includes a bending portion on a distal end side of the insertion section, and a direction of the distal end portion is changed through operation of an operation section.

Incidentally, in the endoscope having the bending portion, built-in components that are easily influenced by bending operation are desirably disposed at respective positions close to the center in a bending tube as much as possible in order to secure durability, workability, and the like of the built-in components in the bending tube. At the same time, favorable displacement of the respective built-in components in the bending tube is not necessarily coincident with favorable displacement of the respective corresponding functional portions at the distal end portion. Thus, in the endoscope of this type, measures such as appropriate change of the displacement of the built-in components in the bending tube, inside the bending portion are performed. For example, Japanese Patent Application Laid-Open Publication No. 2006-288759 discloses a technology in which a light guide that has rigidity lower than rigidity of the other built-in components and has a concern about buckling or the like due to the bending operation is disposed at a position close to the center in the bending tube, in the middle in the insertion axis direction of the bending portion, and is disposed at a position close to an outer circumference in the bending tube in association with the displacement of an illuminating window of the distal end portion, on a distal end side in the insertion axis direction of the bending portion (see FIGS. 11 and 12 in Japanese Patent Application Laid-Open Publication No. 2006-288759 mentioned above).

SUMMARY OF THE INVENTION

An endoscope according to an aspect of the present invention includes: a bending portion provided on a distal end side of an insertion section that extends from a hand side toward a distal end; a signal line of an image pickup unit that is inserted into the insertion section; a wire conduit inserted into the insertion section, and including a drive wire that is inserted into the wire conduit and is advanced and retracted in an axial direction to drive an optical system of the image pickup unit; and a protective member provided to cover an outer circumference of the wire conduit, in which the signal line and the wire conduit are disposed to overlap and intersect with each other in a radial direction in a bending tube configuring the bending portion, the wire conduit is disposed close to a center in the bending tube, on a side closer to a proximal end side than a region where the wire conduit and the signal line intersect with each other, and the protective member is removed from a partial region that includes the region where the wire conduit and the signal line intersect with each other.

DETAILED DESCRIPTION OF THE PREFERRED EMBODIMENT(S)

Figure 1:
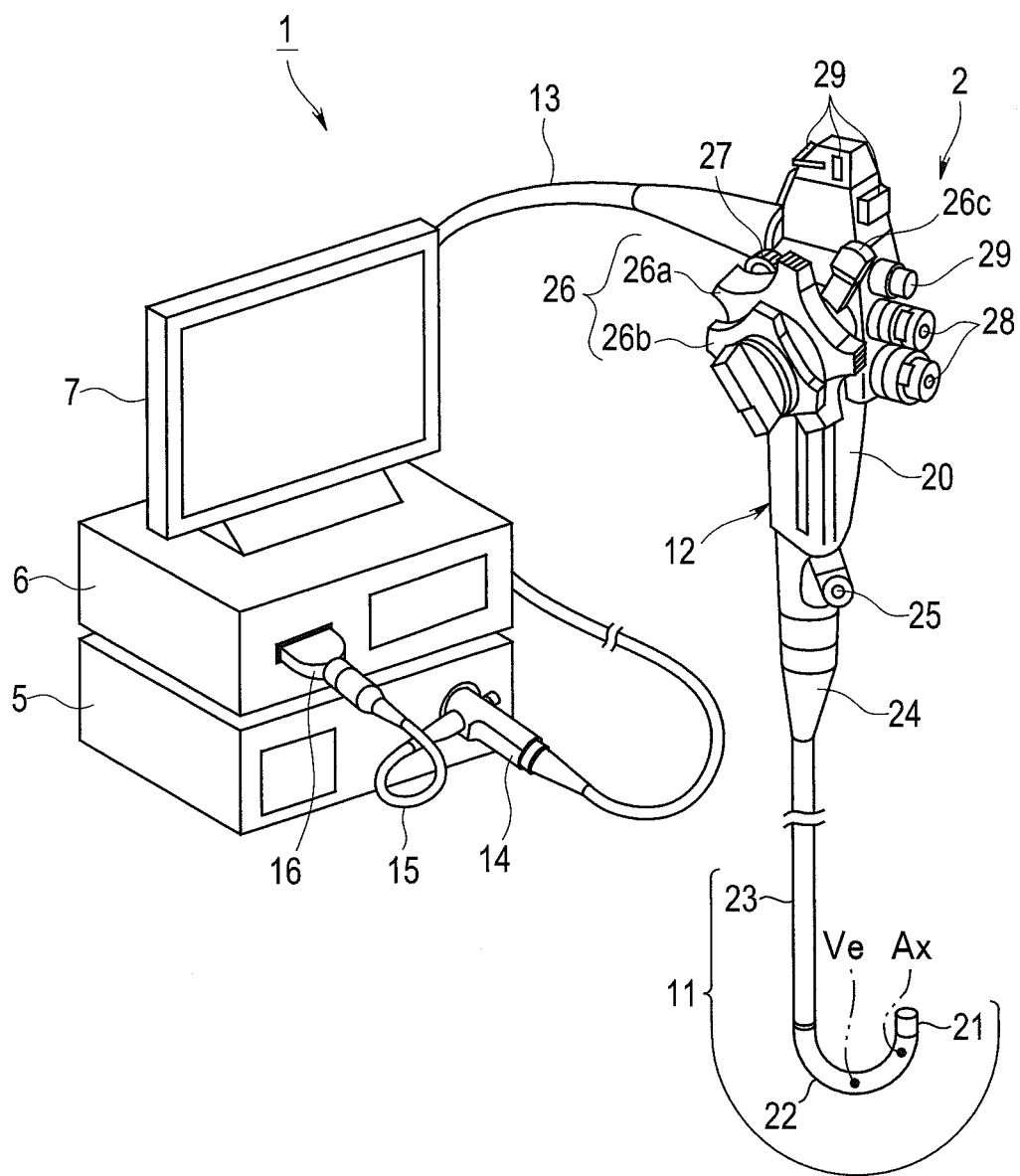
FIG. 1 is a schematic configuration diagram of an endoscope system.
Figure 2:
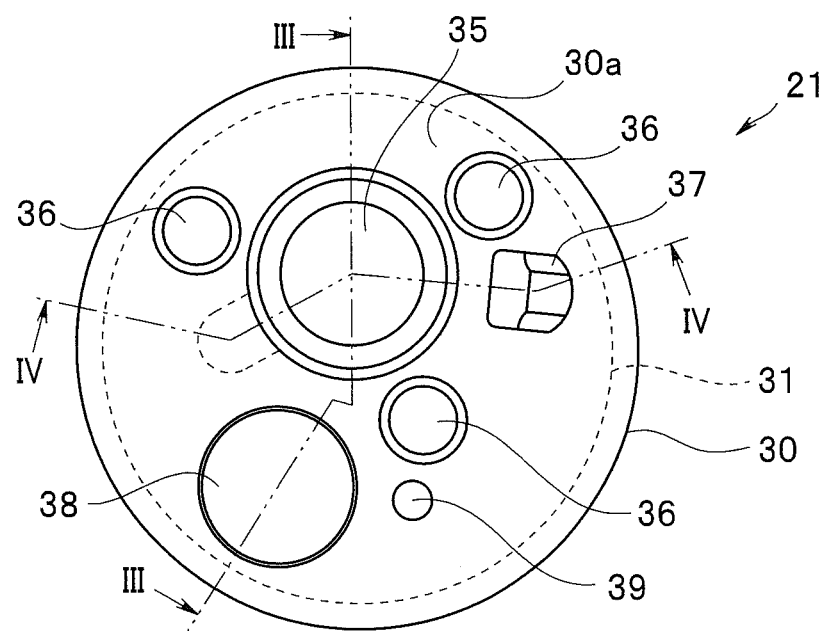
FIG. 2 is an end view of a distal end portion.
Figure 3:
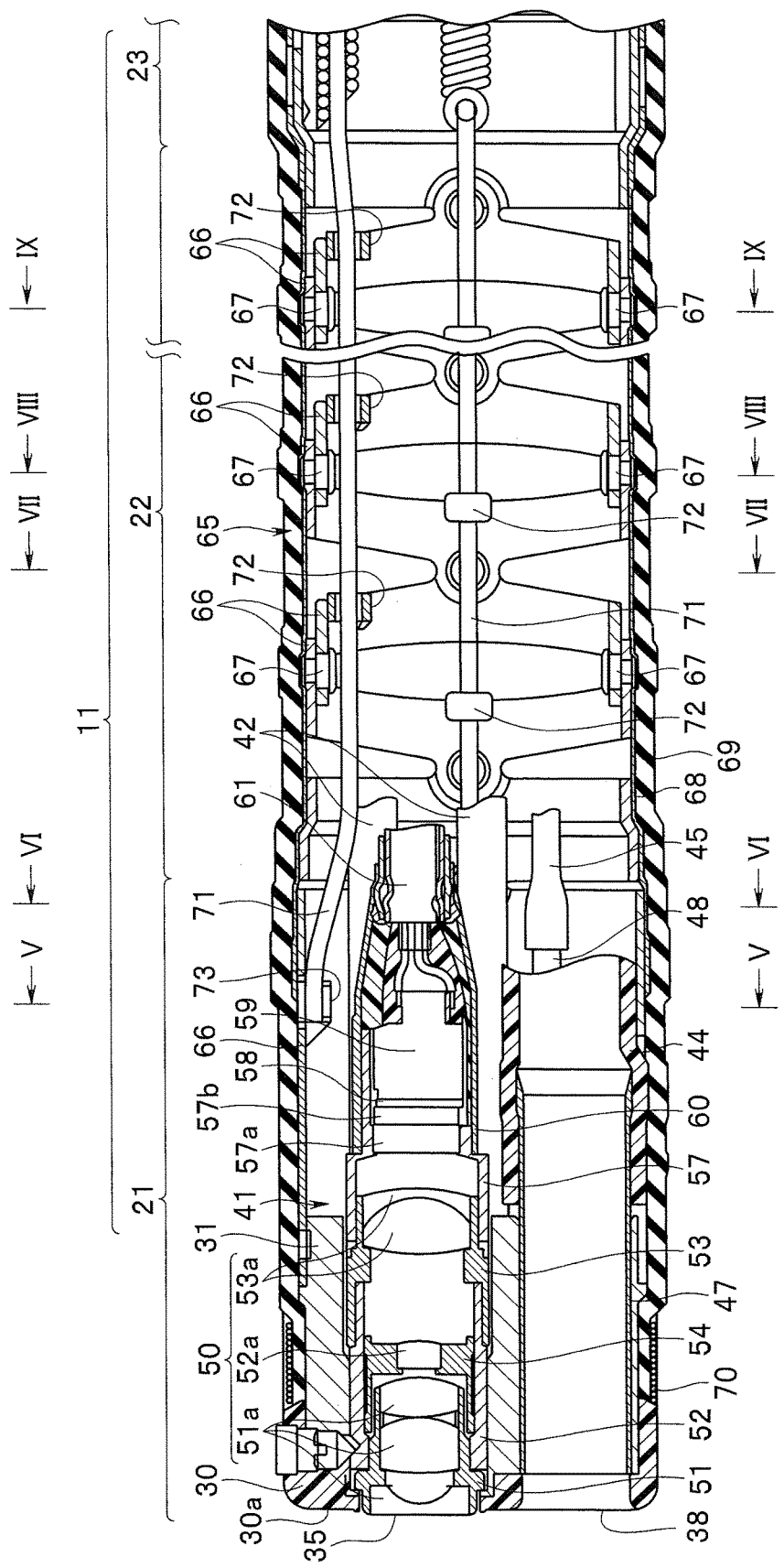
FIG. 3 is a sectional diagram taken along a line III-III of FIG. 2.
Figure 4:
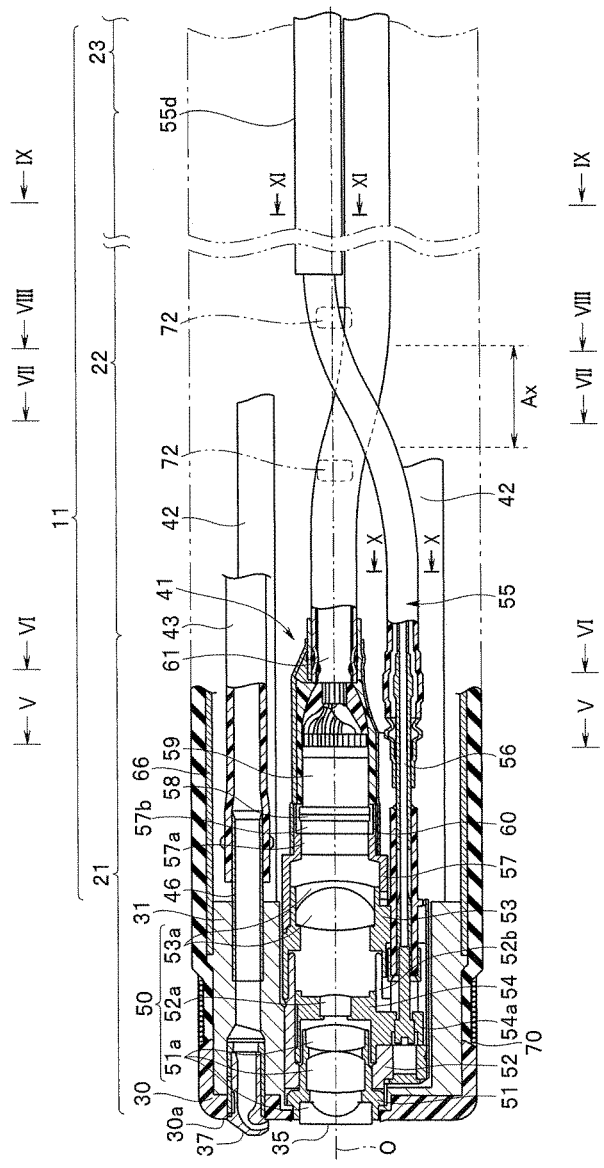
FIG. 4 is a sectional diagram taken along a line IV-IV of FIG. 2.
Figure 5:
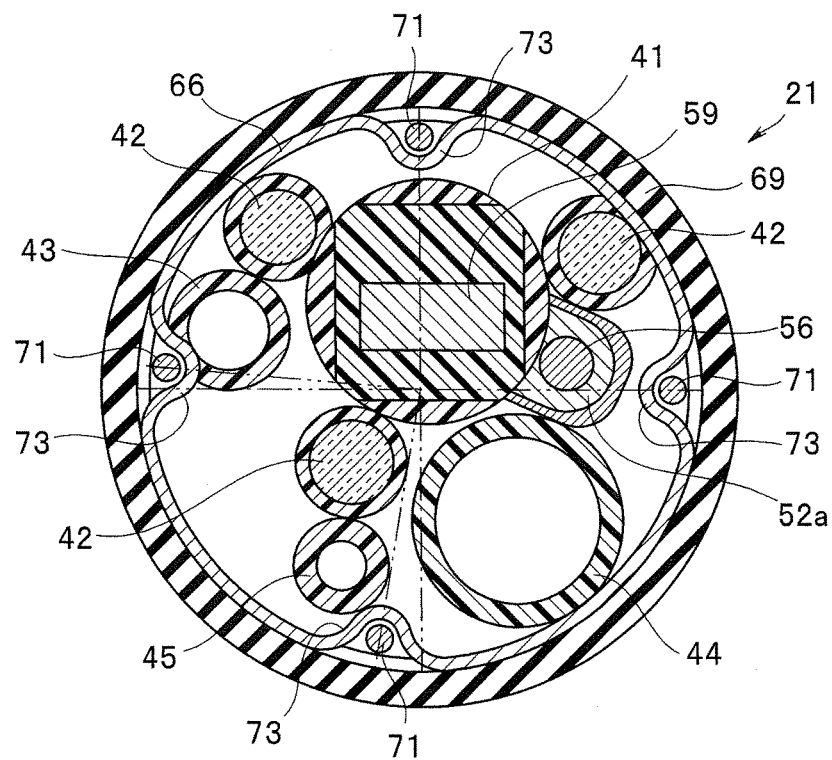
FIG. 5 is a sectional diagram taken along a line V-V of FIGS. 3 and 4.
Figure 6:
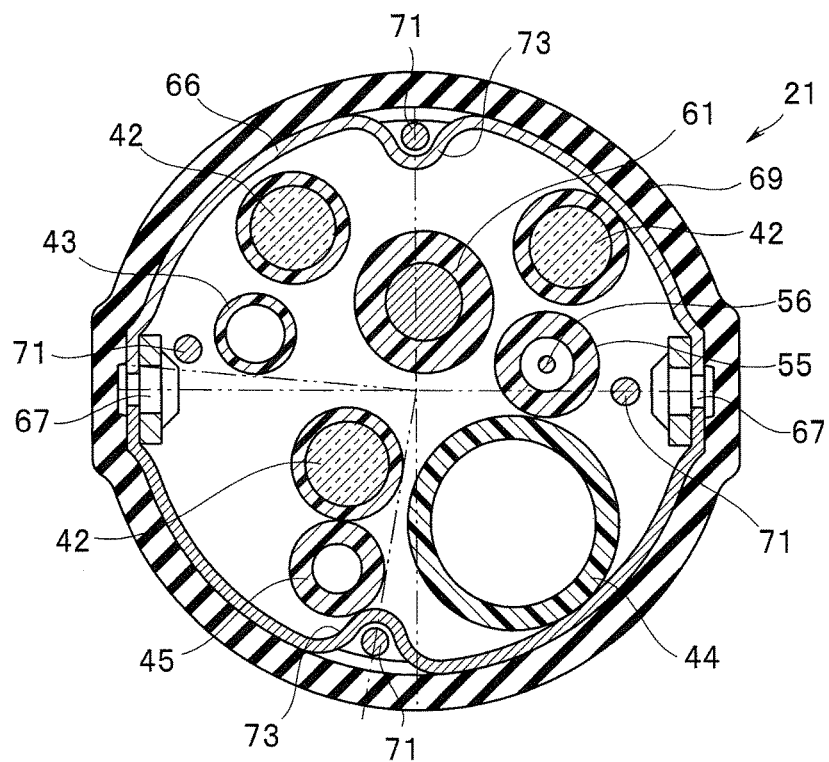
FIG. 6 is a sectional diagram taken along a line VI-VI of FIGS. 3 and 4.
Figure 7:
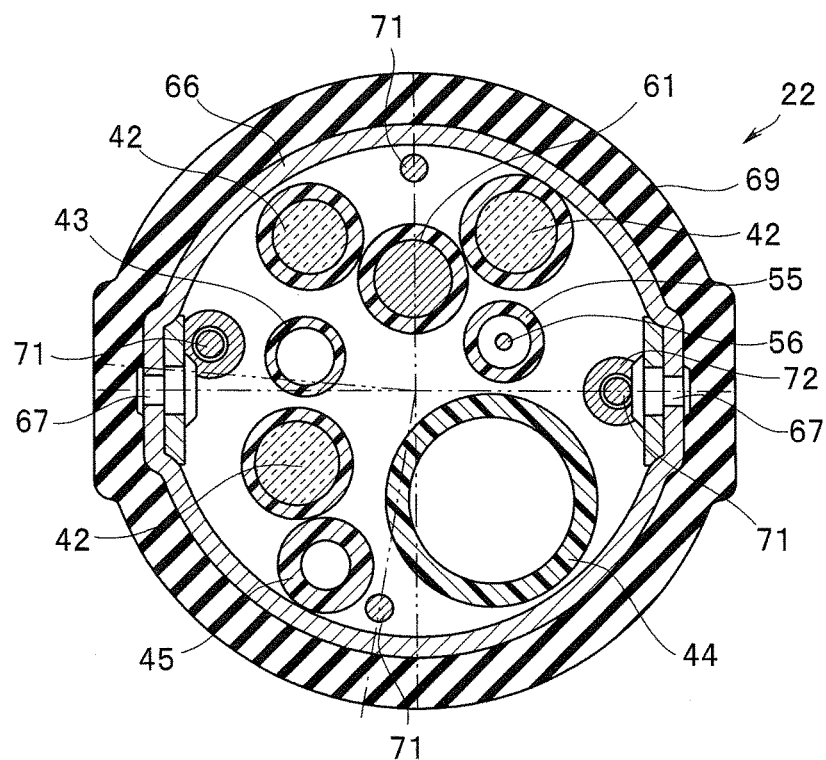
FIG. 7 is a sectional diagram taken along a line VII-VII of FIGS. 3 and 4.
Figure 8:
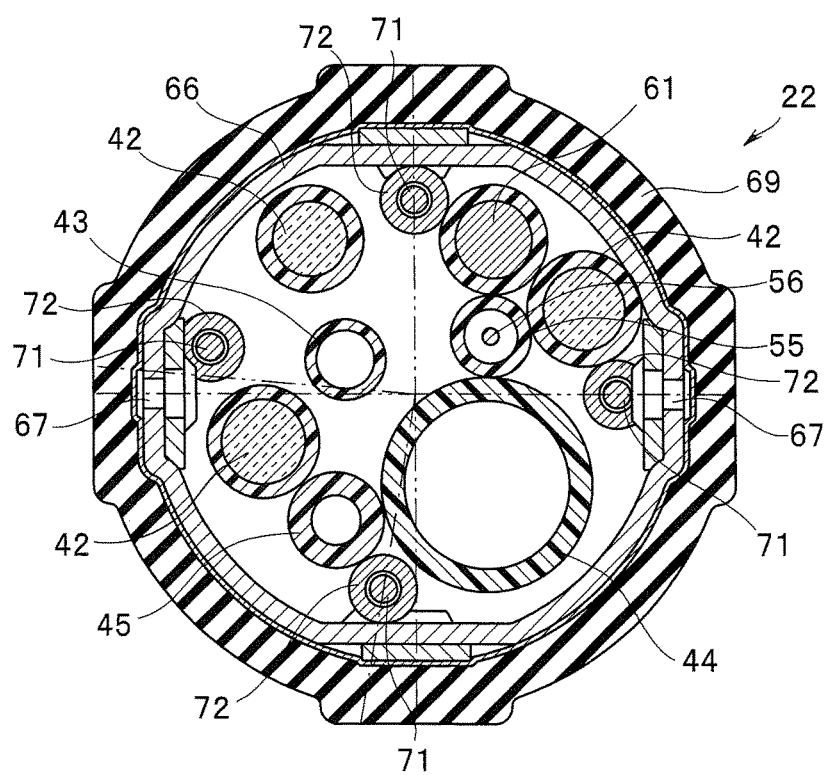
FIG. 8 is a sectional diagram taken along a line VIII-VIII of FIGS. 3 and 4.
Figure 9:
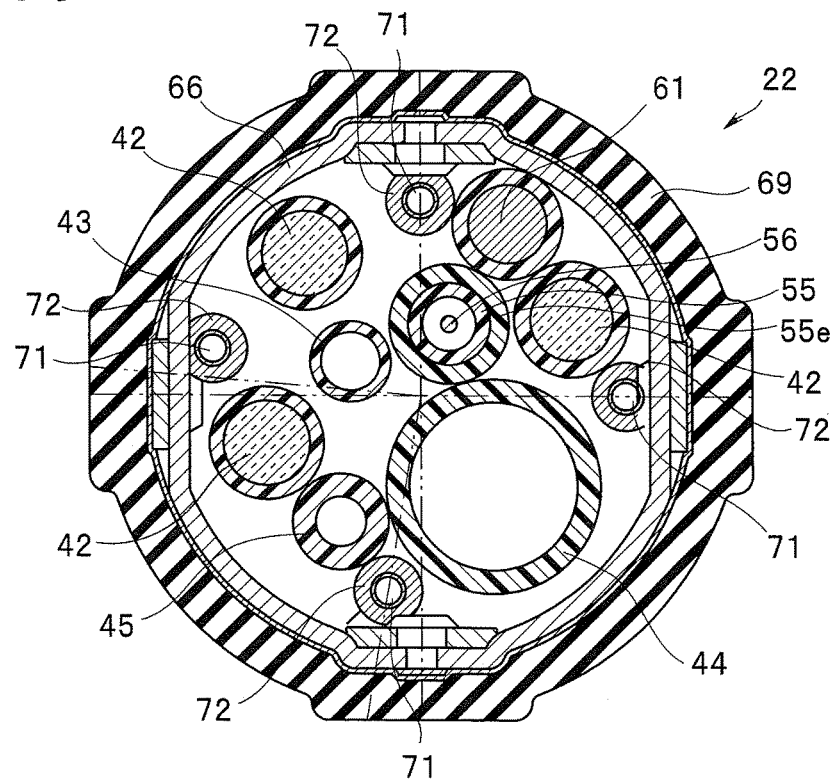
FIG. 9 is a sectional diagram taken along a line IX-IX of FIGS. 3 and 4.
Figure 10:
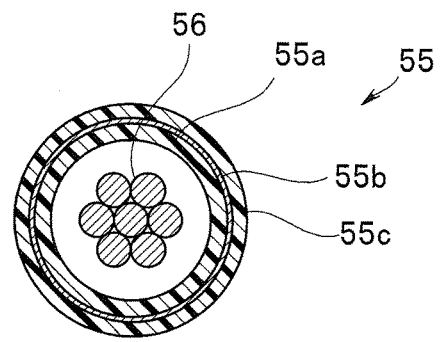
FIG. 10 is an enlarged sectional diagram taken along a line X-X of FIG. 4.
Figure 11:
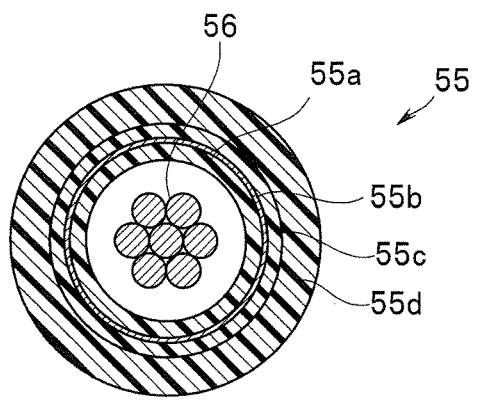
FIG. 11 is an enlarged sectional diagram taken along a line XI-XI of FIG. 4.

In the following, some embodiments of the present invention are described with reference to drawings. The drawings are related to an embodiment of the present invention. FIG. 1 is a schematic configuration diagram of an endoscope system, FIG. 2 is an end view of a distal end portion, FIG. 3 is a sectional diagram taken along a line III-III of FIG. 2, FIG. 4 is a sectional diagram taken along a line IV-IV of FIG. 2, FIG. 5 is a sectional diagram taken along a line V-V of FIGS. 3 and 4, FIG. 6 is a sectional diagram taken along a line VI-VI of FIGS. 3 and 4, FIG. 7 is a sectional diagram taken along a line VII-VII of FIGS. 3 and 4, FIG. 8 is a sectional diagram taken along a line VIII-VIII of FIGS. 3 and 4, FIG. 9 is a sectional diagram taken along a line IX-IX of FIGS. 3 and 4, FIG. 10 is an enlarged sectional diagram taken along a line X-X of FIG. 4, and FIG. 11 is an enlarged sectional diagram taken along a line XI-XI of FIG. 4.

In an endoscope system 1 illustrated in FIG. 1, a main part is configured to include: an endoscope 2 serving as an insertion device; a light source apparatus 5; a video processor 6 serving as a CCU (camera control unit); and a monitor 7.

As illustrated in the same drawing, the endoscope 2 is configured to include: an elongated insertion section 11 that is to be inserted into a site to be observed; an operation section 12 that is continuously provided with a proximal end portion of the insertion section 11; a universal cable 13 that extends from a side surface from the operation section 12; a light source connector 14 that is provided at an extending end part of the universal cable 13; an electric cable 15 that extends from a side part of the light source connector 14; and an electric connector 16 that is provided at an extending end of the electric cable 15.

Note that the light source connector 14 is detachably connected to the light source apparatus 5. Also, the electric connector 16 is detachably connected to the video processor 6.

The insertion section 11 includes a distal end portion 21 on the distal end side, and a bending portion 22 serving as a bendable moving portion is continuously provided at a rear part of the distal end portion 21. Further, a long flexible tube portion 23 that has flexibility and is formed of a soft tubular member is continuously provided at a rear part of the bending portion 22.

The operation section 12 is configured to include: an operation section main body 20 that configures an operation grasping portion; a bend preventing portion 24 that is connected to a proximal end side of the flexible tube portion 23 of the insertion section 11; and a treatment instrument insertion port 25 that is provided near the bend preventing portion 24, as an opening portion of a treatment instrument channel in the insertion section 11.

In the operation section main body 20, a bending operation knob 26 configured to perform bending operation of the bending portion 22 of the insertion section 11 is pivotably provided, and an operation lever 27 configured to move at least some of lenses in an image pickup unit 41 described later (see FIGS. 3 and 4) in an optical axis direction to perform focusing operation is provided. Further, in the operation section main body 20, switches 28 and 29 for various kinds of endoscope functions, or other components are provided. Note that the bending operation knob 26 includes an UD bending operation knob 26a and an RL bending operation knob 26b that are disposed to be overlapped with each other. The UD bending operation knob 26a is to perform bending operation of the bending portion 22 in a vertical direction. The RL bending operation knob 26b is to perform bending operation of the bending portion 22 in a lateral direction. Also, a lock lever 26c that restricts or releases the pivoting operation of the UD bending operation knob 26a by being operated is provided between the UD bending operation knob 26a and the operation section main body 20.

The light source apparatus 5 supplies illuminating light to a light guide bundle 42 (see FIGS. 3 to 9) that is provided in the endoscope 2. In other words, the light guide bundle 42 is provided inside the universal cable 13, the operation section 12, and the insertion section 11 of the endoscope 2 of the present embodiment. The light source apparatus 5 supplies, through the light guide, illuminating light to an illumination optical system that configures an illuminating window described later of the distal end portion 21. The illuminating light is diffused by the illumination optical system, and is applied to a site to be examined.

The video processor 6 converts image data that has been picked up by the endoscope 2, into a video signal, and displays a video on the monitor 7. Further, the video processor 6 receives operation signals of the switches 29 that are disposed in the operation section 12 of the endoscope 2. In response to the signals, the video processor 6 controls the light source apparatus 5, drives an unillustrated compressor, or feeds air to an unillustrated water feeding tank, thereby performing air/water feeding control of air, or water or saline serving as cleaning water in the water feeding tank to feed the air and the water to the distal end portion 21 through an air/water feeding channel of the insertion section 11. Note that the switches 28 are mechanical switches operated by a user in the air/water feeding.

Next, a detailed configuration of the insertion section 11 mainly configured of the distal end portion 21 and the bending portion 22 is described with reference to FIG. 2 to FIG. 9.

As illustrated in FIGS. 3 and 4, the distal end portion 21 is configured to include a distal end cover 30, and a distal end rigid member 31 that is continuously provided on a proximal end side of the distal end cover 30.

The distal end cover 30 is configured of a resin member in which a plurality of hole portions are formed on a distal end surface 30a. As illustrated in FIG. 2, the hole portions of the distal end cover 30 are respectively provided with, as respective functional portions of the endoscope 2: an observation window 35; a plurality of (for example, three) illumination windows 36; a cleaning nozzle 37 to feed air or water mainly to the observation window 35; a channel opening portion 38 of the treatment instrument channel; and an auxiliary water feeding port 39 to perform forward water feeding mainly to the site to be observed.

In the present embodiment, the observation window 35 is disposed at substantially center of the distal end surface 30a. Also, the respective illumination windows 36 are disposed at positions surrounding the observation window 35 on the distal end surface 30a. Further, the cleaning nozzle 37 is disposed at a position adjacent to the observation window 35 on the distal end surface 30a. The channel opening portion 38 is disposed at a position offset from the observation window 35 on the distal end surface 30a. Also, the auxiliary water feeding port 39 is disposed at a position adjacent to the channel opening portion 38 on the distal end surface 30a.

As illustrated in FIGS. 3 and 4, the distal end rigid member 31 is configured of a rigid metal member having insertion holes that are formed at positions corresponding to the respective hole portions of the distal end cover 30. To configure the above-described respective functional portions, an image pickup unit 41 is inserted into and held by the corresponding insertion hole of the distal end rigid member 31, and respective distal end sides of the light guide bundle 42, a cleaning tube 43, a treatment instrument insertion channel 44, and an auxiliary water feeding tube 45 are connected to the respective corresponding insertion holes of the distal end rigid member 31 through a light guide bundle holding tube (not illustrated), a cleaning tube connection tube 46, a treatment instrument channel connection tube 47, and an auxiliary water-feeding tube connection tube 48.

The image pickup unit 41 of the present embodiment is configured to include a lens optical system 50 that has a focusing function with respect to a site to be observed. As illustrated in FIGS. 3 and 4, in the lens optical system 50, a main part is configured of a first lens frame 51, a second lens frame 52, and a third lens frame 53 that are sequentially coupled with one another. The first lens frame 51 holds a first lens group 51a that has, at a distal end, an objective lens configuring the observation window 35. The second lens frame 52 is disposed on a proximal end side of the first lens group 51a and holds a second lens group 52a. The third lens frame 53 is disposed on a proximal end side of the second lens group 52a and holds a third lens group 53a.

In the present embodiment, the second lens group 52a is held by the second lens frame 52 through a movable lens frame 54 that is advanceable and retractable in the optical axis direction. An operation rod portion 54a is provided on a side part of the movable lens frame 54, and the operation rod portion 54a projects outside the lens frame through a slit 52b that is formed in the second lens frame 52. The operation rod portion 54a is coupled with a distal end side of a wire 56 that projects from a conduit (a wire conduit) 55 that serves as a built-in component inserted into the insertion section 11. In contrast, the other end side of the wire 56 is coupled with the operation lever 27 inside the operation section 12. Thus, the movable lens frame 54 causes the second lens group 52a to advance or retract in conjunction with swinging operation of the operation lever 27.

Also, the proximal end side of the third lens frame 53 is coupled with a device frame 57, and the device frame 57 holds an image pickup device 58 such as a CCD or a CMOS, through a cover glass 57a and a glass lid 57b. The proximal end side of the device frame 57 is continuously provided with a shield frame 60 that houses the image pickup device 58 integrally with a circuit substrate 59. Also, in the shield frame 60, the circuit substrate 59 is electrically connected to a distal end side of the image pickup cable 61 that serves as a built-in component inserted into the insertion section 11. In contrast, the other end side of the image pickup cable 61 is connected to the video processor 6 from the insertion section 11, through the operation section 12, the universal cable 31, and the electric connector 16.

The bending portion 22 is configured to include a bending tube 65 in which a plurality of bending pieces 66 are pivotably provided continuously through rivets 67. Out of the bending pieces 66, the bending piece 66 located at the most distal end is coupled with a proximal end side of the distal end rigid member 31 inside the distal end portion 21.

Also, an outer circumference of the bending tube 65 is covered with a braid 68, and an outer circumference of the braid 68 is covered with a bending rubber 69 serving as an outer skin. A distal end side of the bending rubber 69 is extended to the outer circumference of the distal end rigid member 31, and is provided continuously to the proximal end side of the distal end cover 30. The distal end portion of the bending rubber 69 is fixed to an outer circumferential part of the distal end rigid member 31 with a bobbin bonding portion 70.

The above-described respective built-in components are inserted into the bending tube 65, and for example, four bending operation wires 71 are inserted into the bending tube 65. In the bending tube 65, the middles of the respective bending operation wires 71 are guided by wire guides 72 that are provided at right positions of the respective bending pieces 66. Further, the distal ends of the respective bending operation wires 71 are fixed by a wire stopper 73 that is provided in the bending piece 66 located at the most distal end. The four bending operation wires 71 are pulled and slackened through rotating operation of the respective bending operation knobs 26a and 26b provided in the operation section 12, which allows the bending portion 22 to perform bending operation.

Incidentally, in the endoscope 2 including the above-described image pickup unit 41, the wire 56 in the conduit 55 is easily influenced by bending operation of the bending portion 22. In other words, for example, in a case where the conduit 55 is disposed to be offset from a center axis in the bending tube 65, the wire 56 may be influenced by the bending operation of the bending portion 22 to largely advance and retract in the conduit 55, and may cause the second lens group 52a to advance and retract, although the operation lever 27 is not operated, in some cases. Therefore, in such an endoscope 2, to reduce influence received by the wire 56 from the bending operation, the conduit 55 may be desirably disposed preferentially at a position close to the center in the bending tube 65. From such a viewpoint, for example, as illustrated in FIG. 9, the conduit 55 of the present embodiment is basically disposed at a position close to the center in the bending tube 65, more specifically, at a position closer to the center than the image pickup cable 61 in the bending tube 65.

As illustrated in FIG. 11, the conduit 55 has a basic configuration in which, for example, a resin tube 55a, a metal braid 55b, and a first heat-shrinkable tube 55c with a small thickness are stacked in order from inside. Further, the outer circumference of the conduit 55 of the present embodiment is covered with a second heat-shrinkable tube 55d with a small thickness serving as a protective member, at least in the bending tube 65. The thickness of the second heat-shrinkable tube 55d is adjusted to optimize a filling rate of the built-in components in the bending tube 65. This prevents positional disturbance of the respective built-in components in the bending tube 65 while allowing relative movement of the respective built-in components (see FIG. 9).

On the other hand, as mentioned above, since the observation window 35 of the present embodiment is disposed substantially at the center of the distal end surface 30a, the circuit substrate 59 to which the image pickup cable 61 is connected is disposed at a position close to the center in the distal end portion 21, and the operation rod portion 54a coupled with the wire 56 is disposed to be offset from the center (see FIG. 5). Thus, to dispose the image pickup cable 61 and the conduit 55 in respective association with the circuit substrate 59 and the operation rod portion 54a, the image pickup cable 61 and the conduit 55 are so disposed, in the bending tube 65, as to overlap and intersect with each other in a radial direction of the bending tube 65, as illustrated in FIG. 4 and FIGS. 6 to 8. In other words, the image pickup cable 61 and the conduit 55 are disposed to intersect with each other as cross-symmetrical built-in components. More specifically, the image pickup cable 61 and the conduit 55 are disposed to intersect with each other such that intersections between the image pickup cable 61 and the conduit 55 are present in at least two or more directions, as viewed from a direction perpendicular to an insertion axis O of the insertion section 11 (the bending portion 22).

Also, to eliminate local increase of the filling rate in the bending tube 65 due to the intersection of the image pickup cable 61 and the conduit 55, the second heat-shrinkable tube 55d is removed from a partial region that includes an intersection region Ax where the image pickup cable 61 and the conduit 55 intersect with each other (see FIGS. 4, 6 to 8, and 10).

The intersection region Ax where the image pickup cable 61 and the conduit 55 intersect with each other may be desirably set on a distal end side of the bending portion 22 in the axis O direction. More specifically, the intersection region Ax may be desirably set on a side closer to the distal end side than a bending portion apex Ve at which a radius of curvature becomes the smallest when the bending portion 22 is bent (see FIG. 1).

Also, the second heat-shrinkable tube 55d is extended to the proximal end side (the hand side) in the axis O direction from, as a starting point, the vicinity of the intersection region where the image pickup cable 61 and the conduit 55 intersect with each other. At this time, a starting point at which the conduit 55 is covered with the second heat-shrinkable tube 55d may be desirably set at a position shifted in the axis O direction from the wire guide 72 of the bending operation wire 71 that is closest to the conduit 55 in the radial direction in the bending tube 65, for example, as illustrated in FIG. 4.

According to such an embodiment, in the bending tube 65, the outer circumference of the conduit 55, out of the image pickup cable 61 and the conduit 55 that are cross-symmetrical built-in components disposed to intersect with each other in the radial direction of the bending tube 65, is covered with the second heat-shrinkable tube 55*d* serving as a protective member. In addition, the second heat-shrinkable tube 55*d* is removed from a partial region that includes the region (the intersection region Ax) where the image pickup cable 61 and the conduit 55 intersect with each other. This makes it possible to achieve favorable advancing and retracting movement between the respective built-in components (the image pickup cable 61 and the conduit) without causing disturbance of the displacement of the respective built-in components in bending, even when the built-in components intersect with each other in the bending tube 65.

In other words, for example, in a case where it is necessary to intersect some of the built-in components in the bending tube 65 with each other for the reason that a requirement on displacement of the respective functional portions in the distal end portion 21 is different from a requirement on displacement of the respective built-in components corresponding to the functional portions in the bending tube 65, or other reasons, design of the bending tube 65 is performed with, as a reference, the intersection region Ax in which the filling rate becomes the highest locally, and then, the outer circumference of the conduit 55 is covered with the second heat-shrinkable tube 55*d* and the second heat-shrinkable tube 55*d* is removed from a partial region that includes the region Ax where the image pickup cable 61 and the conduit 55 intersect with each other. This allows for equalization of the filling rate in the intersection region Ax and a region other than the intersection region Ax, thereby accurately preventing disturbance of the displacement of the built-in components in the bending of the bending portion 22 as well as achieving favorable relative advancing and retracting motion of the built-in components associated with the bending operation.

In this case, setting the intersection region Ax on the side closer to the distal end side than at least the bending portion apex Ve makes it possible to maintain the most favorable displacement state for the respective built-in components, near the bending portion apex Ve where the built-in components are most likely influenced by the bending operation. At the same time, it is possible to conform the displacement of the respective functional portions to the displacement of the respective built-in components, on the distal end side (on the side closer to the distal end side than the bending portion apex Ve) where the influence by the bending operation is expected to be relatively small.

Also, the starting point on the distal end side of the second heat-shrinkable tube 55*d* is set at a position shifted from the wire guide 72 of the bending operation wire 71 that is closest to the image pickup cable 61 and the conduit 55 in the radial direction in the bending tube 65. This makes it possible to favorably avoid interference between the wire guide 72 and a bump formed by the second heat-shrinkable tube 55*d*.

Note that the present invention is not limited to the respective embodiments described above, and various modifications and alternations may be made on the present invention and are also within the technical scope of the present invention. For example, in the above-described embodiment, an example of the configuration in which the image pickup cable 61 and the conduit 55 as the built-in components intersect with each other as the cross-symmetrical built-in components, has been described. The cross-symmetrical built-in components are appropriately modified depending on layout required for the bending tube 65 or other requirements. For example, in a case in which the light guide is disposed at a position close to the center in the bending tube in response to a requirement for protecting the light guide preferentially, and difference occurs with displacement of the respective functional portions at the distal end portion due to the displacement of the light guide, the built-in components different in displacement are selected as the cross-symmetrical built-in components, and the present invention is applicable to the components.

Also, the protective member is not limited to the heat-shrinkable tube, and other various protective members are adoptable. In addition, an object to be covered with the protective member is not limited to the above-described embodiment, and two or more built-in components may be covered with the protective member irrespective of whether the built-in components are cross-symmetrical built-in components.

Also, the protective member may be disposed on the distal end side from the intersection region when the configuration illustrated in the above-described embodiment is taken as an example. In addition, the thickness of the protective member may be varied before and after the intersection region. Further, in a case where a gap is provided between the protective member and an object to be protected, the protective member may be fixed by means such as bind bonding.

Further, the built-in components that are inserted into the bending tube and to which the present invention is applied are not limited to the above-described respective built-in components. Alternatively, for example, a wire conduit for forceps uplifting is adoptable in a side-view type endoscope.

What is claimed is:

1. An endoscope, comprising:
    a bending portion provided on a distal end side of an insertion section that extends from a hand side toward a distal end;
    a signal line of an image pickup unit that is inserted into the insertion section;
    a wire conduit inserted into the insertion section, and including a drive wire, the drive wire being inserted into the wire conduit and being advanced and retracted in an axial direction to drive an optical system of the image pickup unit; and
    a protective member provided to cover an outer circumference of the wire conduit, wherein
    the signal line and the wire conduit are disposed to overlap and intersect with each other in a radial direction in a bending tube configuring the bending portion,
    the wire conduit is disposed close to a center in the bending tube, on a side closer to a proximal end side than a region where the wire conduit and the signal line intersect with each other, and
    the protective member is removed from a partial region that includes the region where the wire conduit and the signal line intersect with each other.

2. The endoscope according to claim 1, wherein the region where the wire conduit and the signal line intersect with each other is set on a side closer to a distal end side than a bending portion apex at which a radius of curvature becomes smallest in bending of the bending portion.

3. The endoscope according to claim 1, wherein a starting point of the protective member on the distal end side is set to a position shifted from a wire guide that guides, out of a plurality of bending operation wires each performing bending operation of the bending portion, the bending operation wire that is located at a closest position to the wire conduit in a radial direction in the bending tube.

* * * * *